United States Patent [19]

Mitra et al.

[11] Patent Number: 5,159,064
[45] Date of Patent: * Oct. 27, 1992

[54] PREPARATION OF VIRUS-FREE ANTIBODIES

[75] Inventors: Gautam Mitra, Kensington; Milton M. Mozen, Berkeley, both of Calif.

[73] Assignee: Miles Inc., Elkhart, Ind.

[*] Notice: The portion of the term of this patent subsequent to Aug. 9, 2005 has been disclaimed.

[21] Appl. No.: 471,571

[22] Filed: Jan. 29, 1990

Related U.S. Application Data

[63] Continuation-in-part of Ser. No. 192,044, May 9, 1988, Pat. No. 4,948,877, which is a continuation of Ser. No. 849,612, Apr. 4, 1986, Pat. No. 4,762,714.

[51] Int. Cl.$^5$ .................. C07K 15/06; C12N 9/00; A61K 35/14; A61K 39/395
[52] U.S. Cl. .................. 530/388.1; 424/85.8; 424/530; 435/236; 514/2
[58] Field of Search .................. 530/387, 808, 388.1; 424/85.8, 530; 435/70.21, 236; 514/2

[56] References Cited

U.S. PATENT DOCUMENTS

| 2,897,123 | 7/1959 | Singher | 424/101 |
| 4,396,608 | 8/1983 | Tenold | 424/101 |
| 4,440,679 | 4/1984 | Fernandes et al. | 424/101 |
| 4,640,834 | 2/1987 | Eibl et al. | 424/101 |
| 4,762,714 | 8/1988 | Mitra et al. | 424/101 |
| 4,948,877 | 8/1990 | Mitra et al. | 530/387 |

Primary Examiner—Jacqueline Stone
Attorney, Agent, or Firm—James A. Giblin

[57] ABSTRACT

Antibodies, including monoclonal antibodies (Mabs), can be made substantially free of infectious viruses by storing them in a liquid state at conditions of pH, temperature and time sufficient to inactive substantially all infectious viruses. Preferred inactivation methods involve use of a pH equal to or less than about 4.0 at a temperature of at least about 5° C. for at least about 16 hours.

4 Claims, 1 Drawing Sheet

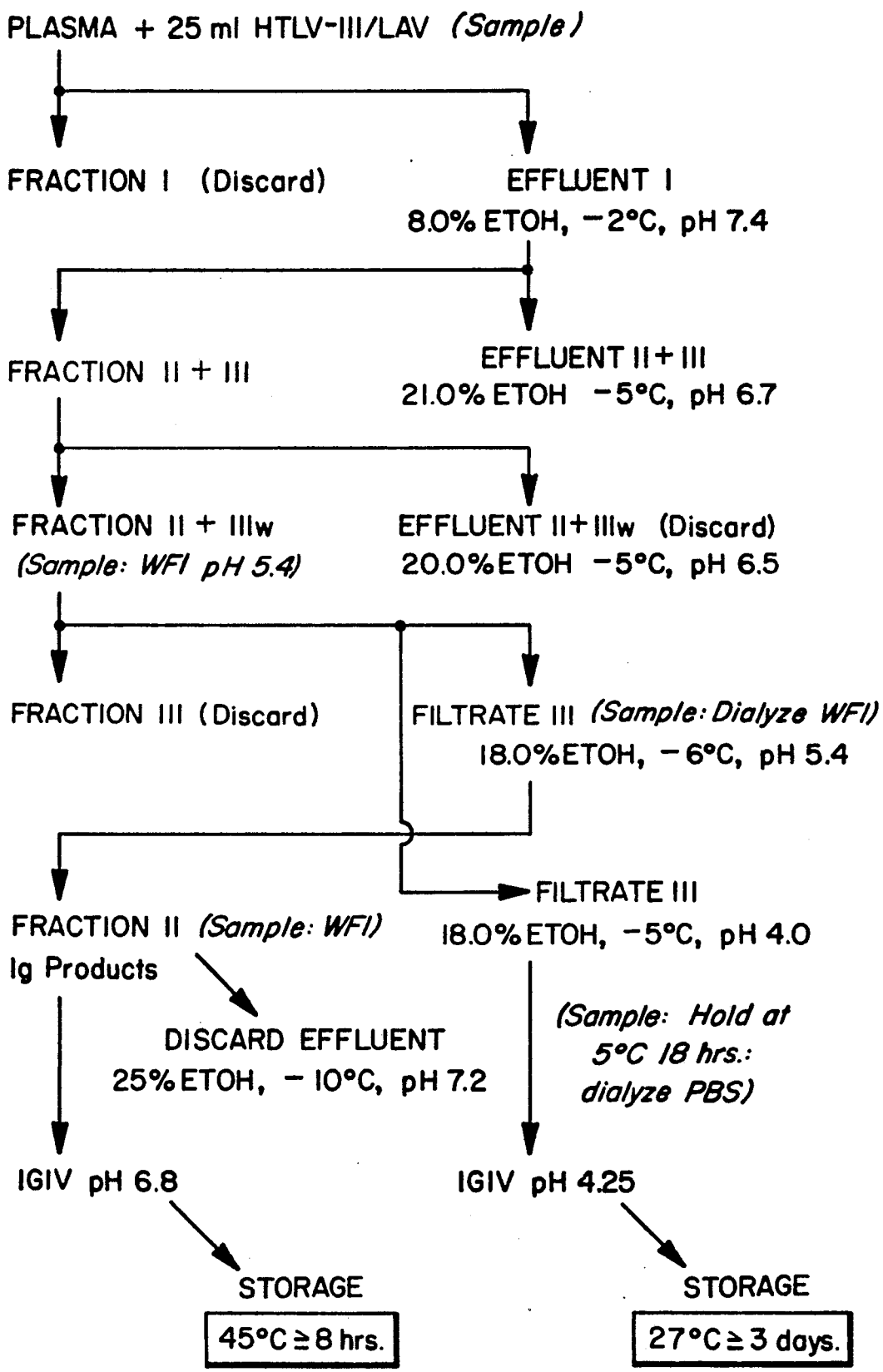

PREPARATION OF VIRUS-FREE ANTIBODIES

This is a continuation-in-part of Ser. No. 07/192,044 filed on May 9, 1988, U.S. Pat. No. 4,948,877, which is a continuation of patent application Ser. No. 06/849,612 filed Apr. 4, 1986, now U.S. Pat. No. 4,762,714.

BACKGROUND OF THE INVENTION

1. Field

This disclosure is concerned generally with the inactivation of viruses and retroviruses in immune serum globulin (ISG) and specifically with the inactivation of such viruses and retroviruses as the LAV strain of an AIDS virus in ISG intended for intravenous (IV) administration.

2. Prior Art

Therapeutic and prophylactic ISG preparations are well known and have been available for many years. ISG is presently obtained in commercial quantities using variations of a blood plasma fractionation technique developed by Cohn et al in the 1940's. Although ISG has been administered intramuscularly (IM) and more recently intravenously (IV), the latter route of administration provides numerous advantages and has gained acceptance as the preferred route of administration.

Initial attempts to render an ISG safe and effective for IV administration (IVIG) focused on eliminating its anticomplement activity. In one approach, for example, this involved chemically modifying the ISG (see U.S. Pat. No. 3,903,262 to Pappenhagen et al). More recently, the ISG has been made suitable for IV administration through careful pH and ionic strength control (see U.S. Pat. No. 4,396,608 and 4,499,073 both to Tenold). It is also known that IVIG preparations can be stabilized with carbohydrates such as maltose (see U.S. Pat. No. 4,186,192 to Fernandes et al). ISG preparations can be further purified using a variety of techniques (see, for example, U.S. Pat. No. 4,272,521 to Zuffi). Various ISG preparations having a relatively high titer to a given antigen are also well known (e.g. tetanus, hepatitis, Rho factor, etc.).

Although ISG products (both IMIG and IVIG) have been considered generally safe, there has been a growing need to assure patients that ISG products do not transmit active viruses such as those associated with hepatitis or, more recently, retroviruses such as that associated with Acquired Immune Deficiency Syndrome (AIDS). The present disclosure is based on work done to address such needs.

Antibodies to a retrovirus associated with the AIDS have been detected in human hepatitis B immunoglobulin (HBIG) (see Tedder, R. S. et al, Safety of immunoglobulin preparation containing anti-HTLV-III, Lancet 1985;1:815) as well as in other commercial lots of immunoglobulins (see Gocke, D. J. et al, HTLV-III antibody in commercial immunoglobulin, Lancet 1986;1:37-8). This observation raised the possibility that immunoglobulin product transmit infectious virus. This concern was heightened by recent reports of non A, non B (NANB) hepatitis in immunodeficient patients who had received infusions of intravenous immunoglobulins prepared from Cohn fraction II (see Webster, A. D. B. et al, Non-A, non-B hepatitis after intravenous gammaglobulin, Lancet 1986;i:322, and Ochs, H. D. et al, Non-A, non-B hepatitis after intravenous gammaglobulin, Lancet 1986;1:322-23).

Based on the above findings, we decided to determine the ability of retroviruses to withstand the various procedures employed in immunoglobulin preparations as well as other procedures. For these experiments, two prototype retroviruses were used: the mouse xenotropic type C retrovirus and the LAV strain of the AIDS retrovirus. Surprisingly, we found that the model retroviruses could be inactivated in ISG prepared by a known fractionation processing technique if that technique is followed by storage at controlled conditions of pH, temperature and time. Details of our method are described below.

SUMMARY OF THE INVENTION

We have found that ISG preparations can be made substantially free of retrovirus such as a LAV strain associated with AIDS by preparing the ISG from pooled plasma using a known processing technique (i.e. Cohn-Oncley cold ethanol process, using at least about 18% ethanol v/v at pH 5.4), followed by storage of the ISG at a pH of less than 5.4, a temperature of at least about 27° C., or at a pH of 6.8 at a temperature of at least about 45° C. for periods sufficient to assure retrovirus inactivation. In preferred embodiments, our ISG preparation is stabilized with a carbohydrate (e.g. maltose) and in a 5% wt./vol. liquid (aqueous) form. It is intended for IV use and is made substantially free (less than 10 infectious virus particles) of the LAV strain of retrovirus associated with AIDS by processing pooled human plasma using the Cohn-Oncley cold ethanol process (about 18% ethanol, pH$\geq$5.4) to obtain ISG followed by storage of the ISG at a pH of about 4.25 for at least about 21 days at a temperature about 27° C. In another embodiment, the ISG may be stored at pH 6.8 for about 45° C., for at least 8 hours to assure the retrovirus inactivation.

BRIEF DESCRIPTION OF THE FIGURE

The FIG. illustrates a flow chart of the steps used in our Cohn-Oncley cold ethanol fractionation of human plasma, including the novel storage conditions disclosed herein.

SPECIFIC EMBODIMENTS

Materials and Methods

The mouse xenotropic type C retrovirus recovered from a New Zealand Black mouse kidney was grown to high titer in mink lung cells (Varnier, O. E. et al, Murine xenotropic type C viruses. V. Biological and structural differences among three cloned retroviruses isolated from kidney cells from one NZB mouse, Virology 1984;132:79-94). Detection was based on a focus assay in mink S+L-cells in which each infectious particle scores as an area of cell transformation (Peeples, P. T., An in vitro focus induction assay for xenotropic murine leukemia virus, feline leukemia virus C, and the feline Primate viruses RI-114/CCC/M-7, Virology 1975;67:288-91). Virus titer was also determined by the induction in cells of the viral core structural protein (page 30) measured by immunofluorescence (see Levy, J. A., Xenotropic type C viruses, Current Topics Microbiol. Immunol. 1978;79:111-212). The use of these assays for detection of mouse C virus in spiking experiments with plasma fractions has previously been described by us (see Levy, J. A. et al, Recovery and inactivation of infectious retroviruses added to factor VIII concentrates, Lancet 1984;ii:722-723 and Levy, J. A. et al, Inactivation by wet and dry heat of AIDS-associated retroviruses during factor VIII purification from plasma, Lancet 1985;i:1456-1457).

LAV was cultured and obtained from the Centers for Disease Control (CDC) in Atlanta, Ga. Its detection was based on a sandwich enzyme-linked immunoassay (ELISA) previously described (see McDougal, J. S. et al, Immunoassay for the detection and quantitation of infectious human retrovirus, lymphadenopathy-associated virus [LAV], J. Immunol. Methods 1985;76:171-183).

Human plasma samples were spiked with retroviral preparations and fractionated according to classical Cohn-Oncley cold ethanol procedures (see Cohn, E. J. et al, Preparation and properties of serum and plasma proteins. IV. A system for the separation into fractions of protein and lipoprotein components of biological tissues and fluids, J. Am. Chem. Soc. 1946;68:459-75 and Oncley, J. L. et al, The separation of the antibodies, isoagglutinins, prothrombin, plasminogen, and beta-1-lipoprotein into subfractions of human plasma, J. Am. Chem. Soc. 1949;71- 541-50). The fractionation was accomplished through selective precipitations in the cold at various ethanol concentrations and pH values: fraction I at 8% ethanol, −2° C., pH 7.4; fraction II-+III at 21% ethanol, −5° C., pH 6.7; fraction II+IIIw at 20% ethanol, −5° C., pH 6.5; fraction III at 18% ethanol, −6° C., pH 5.4; and fraction II collected at 25% ethanol −10° C., pH 7.2. Residual retroviral levels were determined across the fractionation steps. The pH (range 5.4–4.0) and temperature (range −5° C. to 22° C.) effects on virus infectivity in the presence of ethanol (approximately 18%) were determined with filtrate III. Final container liquid immunoglobulin preparations, in the absence of ethanol, were incubated with retrovirus concentrates at 27° C. and 45° C.; virus infectivity was determined at different time periods.

RESULTS

Infectivity of both the mouse C and AIDS retrovirus was not affected by the addition of these viruses to human plasma at ≦5° C. See Table 1.

TABLE 1

| Effect of Immunoglobulin fractionation procedures on infectious retrovirus added to plasma | | |
|---|---|---|
| Store | Mouse Type C (Total IP) | AIDS Virus LAV (Total $ID_{50}$) |
| Virus alone | $2.0 \times 10^8$ | $2.3 \times 10^5$ |
| Virus + plasma (5° C.) | $2.3 \times 10^8$ | $4.4 \times 10^5$ |
| II + IIIw | $3.8 \times 10^7$ | $4.8 \times 10^4$ |
| Filtrate III | $1.6 \times 10^3$ | $1.7 \times 10^3$ |
| Fraction II | Non-detectable | Non-detectable |

Twenty ml of virus concentrate was added to 200 ml of plasma for the fractionation studies described. The fractionation methods and viral assays are described in the text. Total IP = total infectious particles. Total $ID_{50}$ = $ID_{50}$ (reciprocal of dilution at which 50% of the cultures are positive)×volume.

From plasma to fraction II+IIIw, no more than a 10-fold reduction of virus titer was observed. Preparation of filtrate III from fraction II+IIIw resulted in an approximately 10,000-fold reduction of the mouse type C retrovirus and 10-fold reduction in LAV. Due to dilution, ethanol concentration decreased from 20% v/v to 18% v/v across this fractionation step and the pH was reduced from 6.50 to 5.40. Fraction II precipitation from filtrate III resulted in >1,000-fold reduction in titer of both the infectious mouse and human retroviruses. During this fractionation step, the pH was raised to 7.25 and the ethanol concentration increased to 25%. The 1,000-fold loss of virus infectivity primarily results from virus inactivation (not fractionation) since after extensive dialysis, no infectious virus was measurable in the supernatant corresponding to fraction II (data not shown).

In studying more precisely the effect of pH and temperature on retrovirus inactivation with 18% ethanol, we mixed a quantity of the mouse retrovirus with filtrate III. See Table 2.

TABLE 2

| | Effect of pH and Temperature on Mouse Type C Retrovirus added to Filtrate III (18% Ethanol) | | | | | |
|---|---|---|---|---|---|---|
| | Temperature −5° C. | | | | Temperature 22° C. | |
| Sample | (a) pH 5.4 (Total IP) | (b) pH 4.7 (Total IP) | (c) pH 4.0 (Total IP) | Sample | (d) pH 5.4 (Total IP) | (e) pH 4.0 (Total IP) |
| Virus alone | $6.9 \times 10^6$ | $7.9 \times 10^6$ | $7.9 \times 10^6$ | Virus alone | $4.0 \times 10^8$ | $5.0 \times 10^7$ |
| Virus + filtrate III | $2.9 \times 10^6$ | $3.4 \times 10^5$ | $6.5 \times 10^5$ | Virus + filtrate III | $2.2 \times 10^9$ | $5.5 \times 105$ |
| 2 hours | $3.4 \times 10^5$ | $6.6 \times 10^6$ | $2.0 \times 10^5$ | 3 hours | $2.2 \times 10^8$ | Non-detectable |
| 4 hours | $6.7 \times 10^5$ | $6.7 \times 10^5$ | $2.6 \times 10^5$ | | | |
| 6 hours | $7.8 \times 10^5$ | $6.6 \times 10^5$ | $4.1 \times 10^5$ | | | |

At −5° C., no significant virucidal effect was seen in the pH range of 5.4–4.0 for up to 6 hours (2a, b, c). At 22° C. (ambient), however, at pH 4.0 >100,000 infectious mouse retrovirus particles were inactivated by 3 hours (2e). In contrast, at pH 5.4 under similar conditions, no significant virucidal effect was seen (2d). Similarly, $1.7 \times 10^3$ total $ID_{50}$ of LAV that was in a filtrate III solution at pH 4.0 and held at +5° C. for 18 hours, was reduced in titer to non-detectable level (data not shown). It therefore appears that the presence of 18% ethanol in plasma fractions at pH 5.4 is not markedly virucidal for these viruses in the temperature range of −5° C. to 22° C. Only when the pH is lowered (pH 4.0) concomitant with a raise in temperature (≧5° C.), significant virus inactivation observed. For LAV, the following conditions were sufficient for a 1,000-fold reduction in infectious virus: ethanol 18%, pH 4.0, temperature +5° C., time 18 hours (data not shown). For the mouse type C retrovirus, >10,000-fold reduction was measured under similar treatment conditions. To determine the effect on AIDS virus of pH and temperature of the final product, final container liquid immunoglobulin preparations (protein concentration 5% w/v) were incubated with LAV (Table 3). At 27° C., between 103–104 of total $ID_{50}$ were inactivated by 3 days for the immunoglobulin preparations of both pH 6.8 and pH 4.25. At 45° C.,>10,000 infectious particles were inactivated within 8 hours with the pH 6.8 immunoglobulin preparation. The pH 4.25 immunoglobulin preparation was not tested at 45° C.

DISCUSSION

These experiments were conducted to evaluate the effect on infectious retroviruses of procedures used for immunoglobulin fractionation. The data are important in evaluating the possible risk of AIDS virus contamination of some Ig preparations. The mouse type C retrovirus was used as well as the LAV strain of AIDS virus, because the former can be grown to very high titer and therefore the effect of various procedures can be better evaluated. In addition, a focus assay for the mouse virus allows more precise quantitation.

Unlike the reported complement-mediated lysins of many retroviruses in human serum at 37° C. (see Welsh, R. M. et al, Human serum lysins RNA tumor viruses, Nature 1975;257:612-14), the AIDS virus in the cold (0°-5° C.) is not affected by this mechanism (see Banapour, B. et al, The AIDS-associated retrovirus is not sensitive to lysins or inactivation by human serum, Virology [in press] 1986). The reported virucidal effects of ethanol for LAV have been at ambient temperature (see Spire, B. et al, Inactivation of lymphadenopathy associated virus by chemical disinfectants, Lancet 1984;ii:8-99-901 and Martin, L. S. et al, Disinfection and inactivation of human T lymphotropic virus type III/ lymphadenopathy associated virus, J. Infec. Dis. 1985;152:400403), whereas the data reported here show that these virus inactivating effects are diminished in the presence of plasma at low temperatures ($<5°$ C.). Enhanced inactivation at low pH is demonstrated which again is strongly dependent on temperature. This observation agrees with an earlier report (see Martin, L. S. et al, Disinfection and inactivation of human T lymphotropic virus type III/lymphadenopathy associated virus, J. Infec. Dis. 1985; 152:400-403) indicating increased inactivation of LAV inoculum at pH extremes.

Filtrate III with 18% ethanol at pH 5.4 and at a temperature of $-5°$ C. was not significantly virucidal for retroviruses for extended periods of time. Hence, the 100,000-fold reduction of the mouse type C virus and a 100-fold reduction of LAV from plasma to filtrate III is probably primarily due to fractionation under the processing condition (ethanol range 0-20% v/v, pH range 7.4-5.4) employed at $-5°$ C. The reduction difference between the mouse and the human virus reflects either a greater resistance of the AIDS virus to the processing conditions or a less quantitative assay for this virus. As noted above, the mouse virus can be grown up to high titers and its assay is very reproducible. Its usefulness for fractionation/inactivation studies has been previously reported by us (see Levy, J. A. et al, Recovery and inactivation of infectious retroviruses added to factor VIII concentrates, Lancet 1984;ii:722-723 and Levy, J. A. et al, Inactivation by wet and dry heat of AIDS-associated retroviruses during factor VIII purification from plasma, Lancet 1985;i:1456-1457).

Ethanol concentration is increased to 25% v/v at pH 7.20 for the fraction II precipitation which results in a more than 1,000-fold inactivation of the mouse type C virus and LAV. Since the corresponding effluent was free of infectious virus, true inactivation at the 25% ethanol concentration is most likely involved. A recent report (see Piszkiewicz, D. et al, Inactivation of HTLV-III/LAV during Plasma fractionation, Lancet 1985;ii:1188-89) had shown inactivation of $10^{4.5}$ ID$_{50}$ of the AIDS retrovirus during the precipitation of I+II+III (ethanol 20% v/v, pH 6.9, temperature $-5°$ C.) under conditions in which fraction II+III is precipitated together with fraction I. Our results which isolate these fractions separately do not show such complete LAV inactivation under similar conditions (Table 1). In our study, the samples were extensively dialyzed in PBS prior to ID$_{50}$ assay. In the other report, a 1:10 dilution to a resultant residual ethanol concentration of 2% v/v was used in the assay. Furthermore, it is not possible from the other report to distinguish whether the virus titer was being determined in the precipitate or the supernatant following I+II+III precipitation; hence, a meaningful comparison between the two studies is difficult to make.

Greater than a 1,000-fold drop in AIDS virus infectivity did result after its incubation with purified liquid immunoglobulin preparations at 27° C. for 3 days; pH of the purified immunoglobulin preparations did not seem to have an appreciable effect. A higher incubation temperature (45° C.) demonstrated comparable titer reduction within 8 hours. A "worse case" estimate of 2,000 ID/ml of AIDS virus in large plasma pools has been reported (see Petricciani, J. C. et al, Case for concluding that heat-treated, licensed antihaemophilic factor is free from HTLV-III, Lancet 1985;ii:890-891). The yield of IgG could be as low as 50% of the amount present in plasma together with IgG concentration increase from approximately 1 gm/100 ml in plasma to 5 gm/100 ml in purified product. If the AIDS virus was concentrated without loss of infectivity along with IgG purification, the purified IgG would contain 2,000 ID/ml $\times$ 10 ($2 \times 10^4$ ID/ml) Immunoglobulin purification processes must therefore be able to fractionate/inactivate $2 \times 10^4$ ID/ml of AIDS virus.

No single step in the Cohn cold ethanol process can completely inactivate retroviruses. The effects of fractionation and inactivation taken together through the fractionation cascade could be quite large. LAV recovery from plasma to fraction II is reduced by at least 100,000-fold; pH adjustment to 4.0 at filtrate III (at $+5°$ C.) is as effective for viral inactivation as precipitation of fraction II in the presence of 25% ethanol. An extra margin of safety is provided when the final preparation in liquid form is incubated at 27° C., since these experiments demonstrated that in liquid immunoglobulin preparations, a 1,000-10,000-fold reduction of LAV occurred within 3 days under these conditions. Prince et al, Effect of Cohn fractionation conditions on infectivity of the AIDS virus. N. Eng. J. Med 1986; 314:386-87, have suggested that the long storage of liquid immune serum globulin preparations may contribute to their safety. The studies presented here experimentally validate that AIDS virus are indeed inactivated during liquid storage. See Table 3.

TABLE 3

Effect of pH and Temperature on LAV added to Final Container Liquid Immunoglobulin Preparations

| | Temperature 27° C. | | Temperature 45° C. | |
| --- | --- | --- | --- | --- |
| Sample | pH 6.8 IgG (Total ID$_{50}$) | pH 4.25 IgG (Total ID$_{50}$) | Sample | pH 6.8 IgG (Total ID$_{50}$) |
| Virus + IgG | $1.65 \times 10^4$ | $3.69 \times 10^3$ | Virus + IgG | $1.65 \times 10^4$ |
| 3 days | Non-detectable | Non-detectable | 1 hour | $6.27 \times 10^3$ |
| 12 days | Non-detectable | Non-detectable | 4 hours | $1.65 \times 10^3$ |
| 24 days | Non-detectable | Non-detectable | 8 hours | Non-detectable |
| | | | 20 hours | Non-detectable |

The chance for an infectious retrovirus to survive this fractionation as well as storage of the liquid final preparation, is therefore extremely small, if at all.

The fractionation/inactivation and final container incubation results reported here support the available clinical and epidemiological evidence that therapeutic immunoglobulins prepared by Cohn-Oncley cold ethanol process ($\geq 18\%$ v/v ethanol, pH $\leq 5.4$ at filtrate III) do not transmit AIDS viruses particularly after storage at a pH of 4.25 at a temperature of 27° C. for about 3 days or at pH 6.8 at temperature of 45° C. for at least 8 hours. The conditions of the Cohn-Oncley process i.e., alcohol concentration, pH, temperature, do not in themselves inactivate AIDS virus as recently reported by Prince et al, Effect of Cohn fractionation conditions on infectivity of the AIDS virus, N. Eng. J. Med. 1986;314:386-87. As described, their study was primarily geared towards determining inactivation, and no sequential fractionation was carried out with a virus spike. The present study, in contrast, mimics a true fractionation run and hence portrays a realistic virus carryover estimate involving the sum total of fractionation and inactivation.

It is important to emphasize that variations from classical Cohn approach need to be validated in terms of their virucidal and virus distribution potential since fractionation, ethanol concentration, pH, and temperature all play an important role in virus recovery. It is possible that total log reduction of different viruses could be different and hence it would be difficult to generalize these virus recovery results for other viruses.

FURTHER STUDIES

Further studies with monoclonal antibodies have confirmed that a low pH viral inactivation can be used for the preparation of monoclonal antibodies without adverse effects. This finding is especially important for monoclonal antibodies intended for therapeutic use although it is also of value for monoclonals used for other purposes (e.g., purification, diagnostics, etc.).

One of the advantages of monoclonal antibodies (Mabs) over plasma-derived antibodies (PD Abs) is that Mabs are expected to be free of viruses associated with plasma, especially humanplasma viruses such as hepatitis viruses and humanimmuno deficiency virus (HIV). However, certain viruses are associated with cell lines from which the Mabs are derived.

For example, EBV is Epstein-Barr virus which is a common viral vector utilized for preparation of human-monoclonals. See, for example, U.S. Pat. No. 4,446,465 to Lostrom. The concern here is that EBV is a human pathogen. We have found that exposure at pH 4.0 inactivates it very well without affecting the monoclonal antibody. Visna is a retrovirus and models human retroviruses reasonable well. Since tumerogenic potential for the hybridoma cell lines is a major concern demonstration of Visna inactivation is important. Mouse C (xenotropic) and Rauscher (Ecotropic) are murine retroviruses and their presence in murine cell is not too uncommon.

To determine the effect of pH on viral inactivation, the above Mabs were spiked with EBV, Visna and VSV with the results shown below.

EXAMPLES

*Pseudomonas aeruginosa* monoclonals

Mabs of the type described in U.S. Pat. No. 4,834,965 to Siadak et. al were incubated at a pH of 4.0 for at least 16 hours at 5° C. as an initial step in their overall purification.

I.

TABLE 4

Summary of Viral Inactivation/Clearance During PsMab IgM Purification

| Purification Step | Virus Reduction (Logs) EBV |
| --- | --- |
| Incubation pH 4 | 6.4 |

Factor VIII Monoclonals

Mabs identified as C7F7 and specific to human coagulation factor VIII were spiked with Visna virus and also subjected to a viral inactivation at pH 4.0 for various times shown below with the following results shown below.

TABLE 5

Clearance/Inactivation of Visna Virus During C7F7 Monoclonal IgG Purification

IV. Virus Inactivation (pH 4.0) at 5° C.
A. DEAE Eluate + Virus

| TIME 0 (pre-treatment) | 6.0** |
| --- | --- |
| 18 hours | 2.25 |
| 24 hours | 1.5 |
| 42 hours | 1.5 |
| 48 hours | 1.5 |

Note:
Virus added to fresh aliquot of indicated preparation.
*log TCID
**Log TCID/mL
T.C. = Tissue culture

Tumor necrosis factor (TNF) Mabs

Mabs specific to TNF were spiked with the indicted viruses and reduction in titers as noted after exposure to pH 4.0 for 16 hours at 5° C. as shown below.

TABLE 6

Model murine virus clearance during the TNF Mab purification process
Titer Reduction of Indicated Virus (Log)

| Process step | Xenotropic Virus* | | Ecotropic virus** |
|---|---|---|---|
| | Assay 1 | Assay 2 | Assay 2 |
| pH 4.0 exposure for ≧16 | 3.9 | ≧3.6 | ≧12.3 |

*Log FFU, based on mink lung (S+L−) assay
**Log PFU, based on XC plaque assay

TNF Mag is isolated from fermenter harvests of A10G10 hydridoma cells and processed through a multistep purification process which includes cell separation, polyethylene glycol precipitation, anion exchange chromatography, size exclusion chromatography and hydroxylapatite chromatogrphay. Nonetheless, the level of trace impurities in the purified product needs to be estimated. These include cell substrate DNA, non-IgG murine proteins and media components. Concern for murine retroviruses in hybridoma cell lines has also necessitated the estimation of the clearance of relevant murine model viruses through the various steps of the purification process.

Model viruses representing various axonomic groups have been utilized to evaluate the ability of the purification process to fractionate and/or inactivate them. The overall clearance of relevant murine retroviruses included a low pH retrovirus inactivation step with virus titer reduction of $\geq 10^{3.6}-10^{4.1}$.

pH 4.0 was critical in this respect because further lowering of pH, although effective in retrovirus inactivation, results in loss of functional activity of the Mab.

CONCLUSION

This application is especially directed to inactivation of both known and unknown viruses associated with continuous (immortal) cells lines. These cell lines are known to those skilled in the art and includes hybridomas, transformed cells, genetically engineered cells, etc.

From the above exaple, it can be seen that exposure of various Mabs to a pH of about 4 for at least about 16 hrs at a temperature of at least about 5° C. is effective in inactivating viruses (decrease in viral titer of at least $10^{3.6}$ fold). It is proposed that this approach would be effective in inactivating retroviruses and yet unknown viruses, particularly unknown retroviruses.

However, given the above disclosure, it is throught that variations will occur to those skilled in the art. Accordingly, it is intended that the scope of the invention disclosed should be limited only by the following claims.

We claim:

1. A method of inactivating viruses in a solution of one or more monoclonal antibodies comprising the step of subjecting the solution to a pH of about 4.0 at a temperature of at least about 5° C. for at least about 16 hours to inactivate the viruses.

2. The method of claim 1 wherein in the antibodies are selected from the group consisting of anti-*Pseudomonas aeruginosa* monoclonal antibodies, anti-factor VIII monoclonal antibodies and anti-TNF monoclonal antibodies.

3. The method of claim 1 wherein the virus inactivated is selected from EBV, Visna, xenotropic and murine ecotropic viruses.

4. The method of claim 1 wherein the virus is a retrovirus.

* * * * *